United States Patent [19]

Hundt et al.

[11] 4,123,384

[45] Oct. 31, 1978

[54] CONTROL SERUM CONTAINING ALKALINE PHOSPHATASE OF CONSTANT ACTIVITY

[75] Inventors: Dieter Hundt, Percha, über Starnberg; Wolfgang Gruber, Tutzing-Unterzeismering; Michael Klarwein, Garmisch-Partenkirchen; Peter Roeschlau, Seeshaupt, all of Germany

[73] Assignee: Boehringer Mannheim GmbH, Mannheim-Waldhof, Germany

[21] Appl. No.: 715,021

[22] Filed: Aug. 16, 1976

[30] Foreign Application Priority Data

Aug. 20, 1975 [DE] Fed. Rep. of Germany ....... 2537127

[51] Int. Cl.$^2$ .................... C09K 3/00; G01N 31/14; G01N 33/16
[52] U.S. Cl. .................... 252/408; 23/230 B; 195/103.5 R; 424/2; 424/3
[58] Field of Search ................ 195/103.5 R; 252/408; 23/230 B; 424/2, 3

[56] References Cited

U.S. PATENT DOCUMENTS

| | | | |
|---|---|---|---|
| 2,999,793 | 9/1961 | Babson | 195/103.5 R |
| 3,425,912 | 2/1969 | Deutsch et al. | 195/103.5 R |
| 3,466,306 | 9/1969 | Babson | 195/103.5 R |
| 3,595,756 | 7/1971 | Steciw | 195/103.5 R |
| 3,723,579 | 3/1973 | Hammer | 195/103.5 R |
| 3,728,226 | 4/1973 | Louderback | 195/103.5 R |
| 3,853,465 | 12/1974 | Rush et al. | 252/408 |
| 3,876,375 | 4/1975 | Maurukas | 252/408 |
| 3,905,872 | 9/1975 | Forgione | 195/103.5 R |
| 3,926,735 | 12/1975 | Monte et al. | 195/103.5 R |

OTHER PUBLICATIONS

Massion, C. G., et al., Clin. Chem., vol. 18, No. 4, pp. 366–373, (1972).
Trotman, C.N.A., et al., Biochem. J., vol. 124 (1), pp. 25–30, (1971).
Blagova, S. I., C. A., vol. 82, 138071y, (1973).
Berman, Sh. A., C. A., vol. 81, 75131z, (1974).
Saito, T., et al., C. A., vol. 80, 56202m, (1974).
Stilinovic, Z., et al., C. A., vol. 77, 60413m, (1972).
Ribas-Ozonas, B., et al., C. A., vol. 75, 86752e, (1971).
Stilinovic, Z., et al., C. A., vol. 73, 53407b, (1970).
Chappelet, D., et al., C. A., vol. 73, 84155x, (1970).

*Primary Examiner*—Benjamin R. Padgett
*Assistant Examiner*—T. S. Gron
*Attorney, Agent, or Firm*—Burgess, Dinklage & Sprung

[57] ABSTRACT

The activity of alkaline phosphatase in aqueous solution, especially in reconstituted serum, is kept constant by adding to the phosphatase-containing solution $Mn^{2+}$ or $Cd^{2+}$ ions, preferably to an end concentration of 0.05 to 0.5 mMol/liter of $Mn^{2+}$ or 0.05 to 0.1 mMol/liter of $Cd^{2+}$. Control serums comprising the $Mn^{2+}$ and/or $Cd^{2+}$ ions in human or animal serum or serum-like compositions are also provided.

16 Claims, No Drawings

CONTROL SERUM CONTAINING ALKALINE PHOSPHATASE OF CONSTANT ACTIVITY

The present invention is concerned with a process for keeping constant the activity of alkaline phosphatase in aqueous solution, especially in reconstituted serum, and is also concerned with a control serum which contains alkaline phosphatase of constant activity.

The determination of alkaline phosphatase plays an important part in clinical-chemical analyses. For the control of such analyses, it is necessary continuously to control the correctness of the analysis by reference to control samples with a definite content of alkaline phosphatase. Such control sera, which, in the case of alkaline phosphatase, are preponderantly human sera, must be capable of providing so-called values for a plurality of components for testing the correctness of the analysis results, which values must be found again in the control serum sample within a given tolerance range. It is a prerequisite that the components in the control serum ready for use are stable. However, in the case of enzymes, the achievement of this stability gives rise to considerable problems.

Alkaline phosphatase (AP) (EC 3.1.3.1) in particular shows, in aqueous solutions, especially in serum, a very marked increase of activity. A report about this astonishing property, which is extremely undesirable in a control serum, is given, for example, in Clin. Chem., 18, 366–373/1972 and Arztl. Lab., 8, 272–279/1972. The rapid increase of the activity, which can amount to more than 100% within a few hours, necessitates the use of only freshly reconstituted control serum.

It is known to prevent this increase of the activity of alkaline phosphatase by heating the reconstituted serum for several hours (6 hours at 37° C.). After expiry of the heating period, a substantial activity constancy of the AP is obtained. However, this process suffers from serious disadvantages. Thus, due to the heating step, as a rule the activity of other enzymes contained in the control serum is substantially reduced or even destroyed so that it cannot be used for the usual control sera which always contain several enzymes. Furthermore, heating for several hours at a precisely maintained temperature is an extremely laborious procedure which is scarcely acceptable in routine analysis.

The present invention provides a process for keeping constant the activity of AP in aqueous solution, especially in reconstituted serum, which does not suffer from the above-mentioned disadvantages and can, in particular, also be employed in the presence of other enzymes, without influencing their activity. Furthermore, the process is to be capable of being carried out with a minimum of expenditure of labor and of providing control sera which, after reconstitution, provide activity values for AP which lie within the tolerance limits for a comparatively long period of time.

The process of the present invention for keeping constant the activity of alkaline phosphatase in aqueous solution, especially in reconstituted serum comprises adding $Mn^{2+}$ and/or $Cd^{2+}$ ions to such a solution.

A favorable range for the desired keeping constant has been found to be, in the case of the $Mn^{2+}$ ions, an addition of 0.05 to 0.5 mMol/liter and, in the case of $Cd^{2+}$ ions, an addition of 0.05 to 0.1 mMol/liter $Mn^{2+}$ and $Cd^{2+}$ are employed in the form of readily water-soluble salts, the anions of which do not exert a disturbing influence on other components in the solution. Therefore, the anions which are preferably employed are those which are otherwise already present in natural serum. These include not only the anions of the widely-distributed mineral acids, such as hydrochloric acid, sulphuric acid, phosphoric acid, boric acid and the like, but also the anions of organic acids, such as acetic acid, lactic acid, citric acid and the like. However, according to the present invention, the anion employed is without importance, provided that it fulfills the above-mentioned conditions.

The appearance of the undesired activity increase of AP occurs especially in serum, regardless of whether the serum is present in a thawed or frozen state. In the case of lyophilized serum, the activity increase occurs as soon as the lyophilisate is again reconstituted with water. Therefore, the process according to the present invention can be employed not only for an already dissolved serum but also preferably in the case of a serum intended to be lyophilized or in the case of the reconstitution of a lyophilized serum. In the case of the preferred embodimental forms, either the lyophilized serum, preferably human serum, contains the necessary content of stabilizer addition according to the present invention or, for the reconstitution thereof, there is employed an aqueous solvent which contains the stabilizing agent. Reconstitution is usually carried out with water and especially with deionized or double distilled water.

The ability to keep constant the AP activity under the above-described conditions is a specific property of $Mn^{2+}$ and $Cd^{2+}$ ions and could not be found in the case of other divalent or other valent metal ions.

The present invention also provides a stabilized control serum with a definite content of AP, together with the usual components of human serum, animal serum or other serum-like compositions and possibly further enzymes present in definite amount, in lyophilized or dissolved form, which contains 0.05 to 0.5 mMol/liter $Mn^{2+}$ and/or 0.05 to 0.1 mMol/liter $Cd^{2+}$, referred to the dissolved form.

As a rule, control sera contain several enzymes, for example, 10 to 20 enzymes, in the case of all of which the activity must be kept constant. Normally, this keeping constant is necessary in order to prevent a loss of activity, only the AP being an exception. An important advantage of a control serum containing AP stabilized according to the present invention is, with regard to the activity constancy, that the activity of the other enzymes present in the serum is hereby not influenced, which means that the stabilizing action is selective for the AP.

A control serum according to the present invention of the above-described type preferably contains:

0.1 to 5 mg. creatinine
0.1 to 5 mg. bilirubin
50 to 300 mg. glucose
0.2 to 5 mg. $Mn^{2+}$ or $Cd^{2+}$
alkaline phosphatase and possibly further enzymes in 100 ml. natural serum or serum-like compositions in lyophilized or dissolved form.

An especially preferred control serum according to the present invention contains:

0.5 to 1.5 mg. creatinine
0.5 to 1.5 mg. bilirubin
100 to 200 mg. glucose
1 to 3 mg. manganese (II) chloride hydrate
acetic acid for the adjustment of the pH to a value of from 6.0 to 7.0 alkaline phosphatase and further enzymes in 100 ml. serum.

Further enzymes which can be present in the control serum in definite amounts include, for example, glutamate-oxalacetate-transaminase (GOT), glutamate-pyruvate-transaminase (GPT), lactate-dehydrogenase (LDH), α-hydroxybutyrate-dehydrogenase (α-HBDH), glucose-6-phosphate dehydrogenase (G-6-PDH), creatine phosphokinase (CPK), glutamate-dehydrogenase (G1-DH), leucine-aminopeptidase (LAP), α-amylase, γ-glutamyl-transpeptidase (γ-GT), aldolase (ALD) and acid phosphatase (SP).

Within the above-given preferred range for the additions of $Mn^{2+}$ or $Cd^{2+}$, there is generally obtained the best constancy of the AP activity. In the case of exceeding the preferred upper limit, there is a danger that the activity decreases, whereas in the case of going below the lower limit, a constancy of the activity can, for all cases, frequently be no longer achieved and a gradual increase of activity is observed. However, this activity increase is still clearly lower than that observed without these additives.

The following Examples 1 to 5 and 7 are given for the purpose of illustrating the present invention, Example 6 being given for comparison:

EXAMPLE 1

A commercially available lyophilized control serum from originally 3 ml. serum with a definite content of alkaline phosphatase was reconstituted with 3 ml. of a 0.1 mM manganese chloride solution in water. The activity of the AP immediately after reconstitution and in definite periods of time thereafter was determined, the reconstituted solution thereby being kept constant at 25° C. The following Table shows the observed percentage change of AP activity:

| 2  | 4  | 6  | 24 | 48 | (hours) |
|----|----|----|----|----|---------|
| +1 | −5 | −3 | −3 | +7 | (%)     |

EXAMPLE 2

Example 1 was repeated but reconstitution took place with 3 ml. of a 0.05 mM manganese chloride solution in water. The percentage activity change was again determined as in Example 1. The following Table shows the observed percentage change of AP activity:

| 2  | 4  | 6  | 24  | 48  | (hours) |
|----|----|----|-----|-----|---------|
| +5 | +6 | +9 | +19 | +24 | (%)     |

EXAMPLE 3

3 ml. human serum, to which were added the desired amounts of enzyme had so much manganese chloride added thereto that the end concentration of manganese was 0.1 mM. The serum was then lyophilized.

The lyophilized serum was reconstituted with 3 ml. double distilled water. The activity change of the AP was determined as described in Example 1. The following Table shows the percentage change of AP activity:

| 2  | 4  | 6  | 24 | 48  | (hours) |
|----|----|----|----|-----|---------|
| +2 | −1 | ±0 | ±0 | +14 | (%)     |

EXAMPLE 4

Example 1 was repeated but reconstitution took place with 3 ml. 0.05 mM aqueous cadmium chloride solution. Subsequently, the percentage of activity of the AP was determined, after storage at +25° C., in the above-described way. The following Table shows the results obtained:

| 2  | 4  | 6  | 24 | 48 | (hours) |
|----|----|----|----|----|---------|
| +2 | ±0 | +1 | +1 | +6 | (%)     |

EXAMPLE 5

Example 4 was repeated but reconstitution took place with 3 ml. 0.1 mM aqueous cadmium chloride solution. The following Table shows the results obtained:

| 2  | 4  | 6  | 24 | 48 | (hours) |
|----|----|----|----|----|---------|
| +2 | +1 | +1 | −4 | +9 | (%)     |

EXAMPLE 6

Example 1 was repeated but reconstitution of the lyophilisate took place with 3 ml. double distilled water. The following Table shows the AP activity change after storage of the reconstituted sample at +25° C.:

| 2   | 4   | 6   | 24  | 48  | (hours) |
|-----|-----|-----|-----|-----|---------|
| +17 | +21 | +27 | +45 | +66 | (%)     |

EXAMPLE 7

Activity-constant control serum 100 ml. human serum were mixed with an enzyme concentrate which contained the enzymes AP, GOT, GPT, CK, LDH, α-HBDH, G1-DH, LAP, γ-GT, acid phosphatase, amylase, aldolase and G-6-PDH. There were also added:
 1 mg. creatinine
 1 mg. bilirubin
 glucose ad 150 mg.
 2 mg. $MnCl_2.4H_2O$
 acetic acid to pH 6.5

The solution obtained was clarified by filtration, filled in 3 ml. portions into small bottles and lyophilized. The lyophilized samples were stored at +4° C.

Upon reconstitution of the control serum with 3 ml. double distilled water and storage of the reconstituted solution at 25° C., within 24 hours there was an AP activity increase of less than 1%.

EXAMPLE 8

(A) The alkaline phosphatase was dissolved in isotonic saline solution. The activity of the AP immediately after reconstitution and in definite periods of time thereafter was determined, the reconstituted solution thereby being kept constant at 25° C. The following Table shows the observed percentage of the AP activity:

| 2  | 4  | 6  | 24 | 48  | (hours) |
|----|----|----|----|-----|---------|
| +3 | −4 | −6 | −8 | −10 | (%)     |

(B) Example 8 A was repeated, but MnCl$_2$ was added to the solution up to a concentration of (a) 0.1 mMol/liter and (b) 0.02 mMol/liter. The following Table shows the percentage change of the AP activity:

|    | 2  | 4  | 6  | 24 | 48 | (hours) |
|----|----|----|----|----|----|---------|
| a) | −1 | ±0 | +1 | ±0 | −1 | (%)     |
| b) | +1 | −1 | −3 | −3 | −5 | (%)     |

It will be understood that the specification and examples are illustrative but not limitative of the present invention and that other embodiments within the spirit and scope of the invention will suggest themselves to those skilled in the art.

What is claimed is:

1. Process for substantially stabilizing the activity of alkaline phosphatase in an aqueous control solution containing a predetermined amount of alkaline phosphatase which process comprises adding at least one of $Mn^{2+}$ and $Cd^{2+}$ ions to said solution, in an amount sufficient to substantially improve the stability of the activity of said alkaline phosphatase therein.

2. Process as claimed in claim 1, wherein $Mn^{2+}$ ions are added to said solution.

3. Process as claimed in claim 1, wherein $Cd^{2+}$ ions are added to said solution.

4. Process as claimed in claim 1, wherein a mixture of $Mn^{2+}$ and $Cd^{2+}$ ions are added to said solution.

5. Process as claimed in claim 1, wherein $Mn^{2+}$ is added to an end concentration of 0.05 to 0.5 mMol/liter.

6. Process as claimed in claim 1, wherein $Cd^{2+}$ is added to an end concentration of 0.05 to 0.1 mMol/liter.

7. Process as claimed in claim 1, wherein the aqueous solution containing alkaline phosphatase is serum.

8. Process as claimed in claim 7, wherein $Mn^{2+}$ and/or $Cd^{2+}$ is added to the serum before lyophilization.

9. Process as claimed in claim 7, wherein $Mn^{2+}$ and/or $Cd^{2+}$ is added to the water used for the reconstitution of lyophilized serum.

10. Aqueous control solution having substantially stabilized alkaline phosphatase activity comprising a predetermined amount of alkaline phosphatase in an aqueous solution and at least one of $Mn^{2+}$ and $Cd^{2+}$ ions dissolved therein, in an amount sufficient to substantially improve the stability of the activity of said alkaline phosphatase therein.

11. Control serum comprising serum or serum substitute having a predetermined amount of alkaline phosphatase therein and containing from 0.05 to 0.5 mMol/liter of $Mn^{2+}$ and/or 0.05 to 0.1 mMol/liter of $Cd^{2+}$.

12. Control serum as claimed in claim 11, wherein said serum is human serum.

13. Control serum as claimed in claim 11, wherein said serum is animal serum.

14. Control serum as claimed in claim 11, also comprising at least one additional enzyme.

15. Control composition as claimed in claim 11, comprising
 0.1 to 5 mg creatinine,
 0.1 to 5 mg bilirubin,
 50 to 300 mg glucose,
 0.3 to 3 mg $Mn^{2+}$, and
 0.6 to 1.2 mg $Cd^{2+}$, and
 alkaline phosphatase
in 100 ml serum or serum substitute.

16. Control serum as claimed in claim 11, comprising
 0.5 to 1.5 mg creatinine,
 0.5 to 1.5 mg bilirubin,
 100 to 200 mg glucose,
 1 to 3 mg manganese (II) chloride hydrate, acetic acid for the adjustment of the pH value of from 6.0 to 7.0, and
 alkaline phosphatase
in 100 ml serum.

* * * * *